United States Patent
Matsue et al.

(10) Patent No.: US 8,238,626 B2
(45) Date of Patent: Aug. 7, 2012

(54) MEDICAL IMAGE DISPLAY APPARATUS

(75) Inventors: Kenji Matsue, Nasushiobara (JP);
Kenichi Niwa, Otawara (JP)

(73) Assignees: Kabushiki Kaisha Toshiba, Tokyo (JP);
Toshiba Medical Systems Corporation,
Otawara-Shi (JP)

(*) Notice: Subject to any disclaimer, the term of this patent is extended or adjusted under 35 U.S.C. 154(b) by 1091 days.

(21) Appl. No.: 12/044,570

(22) Filed: Mar. 7, 2008

(65) Prior Publication Data

US 2008/0219537 A1    Sep. 11, 2008

(30) Foreign Application Priority Data

Mar. 8, 2007    (JP) ................. 2007-058976

(51) Int. Cl.
*G06K 9/38* (2006.01)
*G06T 15/08* (2011.01)

(52) U.S. Cl. .......................... 382/128; 345/424

(58) Field of Classification Search .......... 382/128–133; 345/420, 424, 427
See application file for complete search history.

(56) References Cited

U.S. PATENT DOCUMENTS

| | | | |
|---|---|---|---|
| 2006/0071932 A1* | 4/2006 | Weese et al. | 345/424 |
| 2006/0114254 A1* | 6/2006 | Day et al. | 345/424 |

FOREIGN PATENT DOCUMENTS

| | | |
|---|---|---|
| JP | 8-227449 | 9/1996 |
| JP | 2006-263078 | 10/2006 |
| JP | 2006263078 A * | 10/2006 |

OTHER PUBLICATIONS

U.S. Appl. No. 12/260,395, filed Oct. 29, 2008, Futami, et al.

* cited by examiner

*Primary Examiner* — Jack Berman
*Assistant Examiner* — David E Smith
(74) *Attorney, Agent, or Firm* — Oblon, Spivak, McClelland, Maier & Neustadt, L.L.P.

(57) ABSTRACT

A medical image display apparatus has a dividing unit and a setting unit. The dividing unit divides a range after changing to an overlapping range that a range after changing overlaps a range before changing, and a non-overlapping range that not includes the overlapping range, when a position of the range is changed. The setting unit configured to set a pixel value after changing based on a pixel value constituting a diagnostic image before changing and voxel values along a predefined direction in the non-overlapping range according to a pre-defined condition about a pixel that a position of a voxel value in volume data corresponding to the pixel value constituting the diagnostic image before changing exists in the overlapping range, among each pixels constituting a diagnostic image after changing generated based on the voxel values along the predefined direction in the range after changing.

15 Claims, 4 Drawing Sheets

MEDICAL IMAGE DISPLAY APPARATUS

BACKGROUND OF THE INVENTION

1. Field of the Invention

The present invention relates to a medical image display apparatus for displaying a medical image, and, more particularly, to a medical image display apparatus for displaying a medical image having a thickness in a visual axis direction.

2. Description of the Related Art

A medical image display apparatus displays a medical image of a patient based on volume data obtained by medical image generating apparatuses such as X-ray computed tomography (X-ray CT) apparatuses, magnetic resonance imaging (MRI) apparatuses, and the like. The volume data is generated by overlapping slice images, which are generated by a medical image generating apparatus, in a slice axis direction.

The medical image display apparatus has MPR (Multi Planar Reconstruction) functions. The MPR functions are functions for generating a new image (MPR image) by performing a calculation to the volume data obtained by the medical image generating apparatus, that is, to a slice image group in the slice axis direction according to various arbitrarily designated parameters such as a cross section, a thickness, and the like.

As one of the MPR functions, there is a function for providing a thickness range with a thickness in a visual axis direction and projecting a maximum value, a minimum value, or an average value in voxel values of respective pixels in the thickness range (maximum value projection/minimum value projection/averaging value display) so that all the slice images in the thickness range are displayed as a sheet of image (for example, Japanese Patent Publications No. 8-227449 and No. 2006-263078).

However, in the MPR function described above, it is necessary to refer to all the slice images in the thickness range and to calculate data of the maximum value, the minimum value or the average value in the voxel values of the respective pixels in the slice image group. Thus, according to the MPR function, there is a tendency that a processing time necessary to calculate the data is increased and a display speed is reduced. In particular, when images are continuously displayed while moving a cross sectional position, that is, the thickness range in the visual axis direction little by little, the processing time necessary to calculate the data is increased and the display speed is reduced.

SUMMARY OF THE INVENTION

An object of the present invention, which was made in view of the above circumstances, is to provide a medical image display apparatus capable of increasing a display speed when images are displayed according to the movement of a thickness range.

To solve the above-described problems, the present invention provides a medical image display apparatus comprising: a diagnostic image displaying unit configured to display a diagnostic image generated by voxel values in a predefined range formed along a predefined direction in volume data based on a slice image group; a range dividing unit configured to divide a range after changing as the range to an overlapping range that the range after changing overlaps a range before changing, and a non-overlapping range that not includes the overlapping range, when a position of the range is changed; a pixel value after changing setting unit configured to set a pixel value after changing based on a pixel value constituting a diagnostic image before changing and voxel values along the predefined direction in the non-overlapping range according to a predefined condition about one pixel that a position of a voxel value in the volume data corresponding to the pixel value constituting the diagnostic image before changing exists in the overlapping range, and based on voxel values along the predefined direction in the range after changing according to the predefined condition about the other pixel that the position does not exist in the overlapping range, among each pixels constituting a diagnostic image after changing generated based on the voxel values along the predefined direction in the range after changing; and a diagnostic image generating unit configured to generate the diagnostic image after changing based on the pixel value after changing set by the pixel value after changing setting unit.

To solve the above-described problems, the present invention provides a medical image display apparatus comprising: a diagnostic image displaying unit configured to display a diagnostic image generated by voxel values in a predefined range formed along a predefined direction in volume data based on a slice image group; a range dividing unit configured to divide a range after changing as the range to an overlapping range that the range after changing overlaps a range before changing, and a non-overlapping range that not includes the overlapping range, when a position of the range is changed; a pixel value after changing setting unit configured to set a pixel value after changing based on a total value of voxel values along the predefined direction in the overlapping range obtained by a pixel value constituting a diagnostic image before changing, and based on a total value of voxel values along the predefined direction in the non-overlapping range about each pixels constituting a diagnostic image after changing generated based on the voxel values along the predefined direction in the range after changing; and a diagnostic image generating unit configured to generate the diagnostic image after changing based on the pixel value after changing set by the pixel value after changing setting unit.

DESCRIPTION OF THE PREFERRED EMBODIMENTS

First Embodiment

A first embodiment of a medical image display apparatus of according to the present invention will be explained referring to FIGS. 1 to 6.

Figure 1:
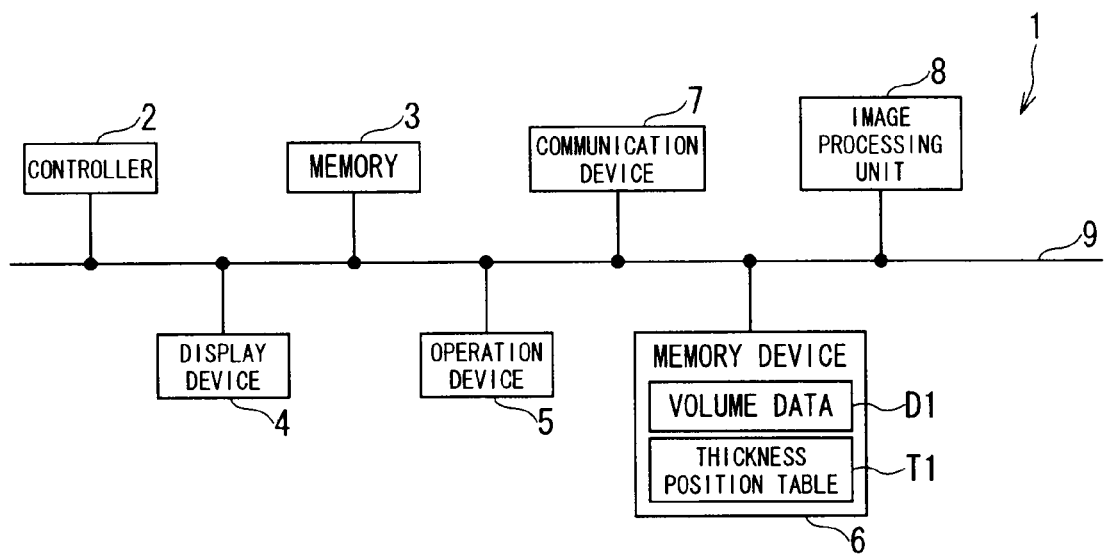
FIG. 1 is a block diagram showing a schematic arrangement of a first embodiment of a medical image display apparatus.

FIG. 1 is a block diagram showing a schematic arrangement of the first embodiment of the medical image display apparatus.

FIG. 1 shows the medical image display apparatus 1 of the first embodiment. As shown in FIG. 1, the medical image display apparatus 1 has a controller 2 such as CPU (central processing unit) and the like for intensively controlling respective units, a memory 3 such as a ROM (read only memory), a RAM (random access memory), and the like, a display device 4 for displaying an image, an operation device 5 for receiving an input operation from an operator, a storage device 6 for storing various types of programs, various types of data, and the like, a communication device 7 for performing a communication to an external apparatus such as a medical image generating apparatus and the like, and an image processing unit 8 for processing an image. These components 2 to 8 are electrically connected to each other through a bus 9.

The controller 2 controls the respective components based on the various types of programs, the various types of data, and the like stored to the memory 3 and the storage device 6. In particular, the controller 2 performs a series of data processings for calculating and processing data, an image display processing for displaying an image, and the like based on the various types of programs, the various types of data, and the like.

The memory 3 stores a start program and the like executed by the controller 2 and also acts as a work area of the controller 2. Note that the start program is read out and executed by the controller 2 when the medical image display apparatus 1 is started.

The display device 4 displays a medical image such as sites and the like of a patient. A liquid crystal display, CRT (Cathode Ray Tube) display, and the like, for example, are used as the display device 4.

The operation device 5 is operated by the operator and receives various types of input operations for starting to an image display, switching an image, and the like. Input devices, for example a mouse, a keyboard, and the like are used as the operation device 5.

The storage device 6 stores the various types of programs, data, and the like and in particular stores volume data D1 as to the respective sites of the patient and a thickness position table T1. Note that the volume data D1 is defined as a slice image group data composed of slice images to illustrate in FIG. 2 later, or as an aggregate of the slice image group data and an interpolated data in FIG. 4 later. A magnetic disc device, a semiconductor disc device (flash memory), and the like, for example, are used as the storage device 6.

The volume data D1 is generated by overlapping slice images generated by a medical image generating apparatus (not shown) such as an X-ray medical image diagnostic (X-ray CT) apparatus, a magnetic resonance image diagnostic (MRI) apparatus, and the like in a slice axis direction. The volume data D1 is transmitted from an external apparatus such as the medical image generating apparatus and the like and stored to the storage device 6 through the communication device 7. Note that a slice interval is, for example, about 1 [mm] to 10 [mm]. Further, the thickness position table T1 is formed of the image processing unit 8 and stored to the storage device 6.

The communication device 7 performs a communication to the external apparatus through a network such as LAN (local area network), The Internet, and the like. A LAN card, a modem, and the like are used as the communication device 7. A database server, the medical image generating apparatus, and the like for storing the volume data D1 are exemplified as the external apparatus. The volume data D1 may be stored from the database to the storage device 6 through the communication device 7 after it is stored once to the data base server. Otherwise, the volume data D1 may be directly stored from the medical image generating apparatus to the storage device 6 through the communication device 7.

The image processing unit 8 has MPR (multi planer reconstruction) functions for performing a calculation to the volume data D1, that is, to a slice image group (aggregate of slice images G) in the slice axis direction according to various types of arbitrarily designated parameters such as a cross section, a thickness, and the like and generates a new image.

Figure 2:
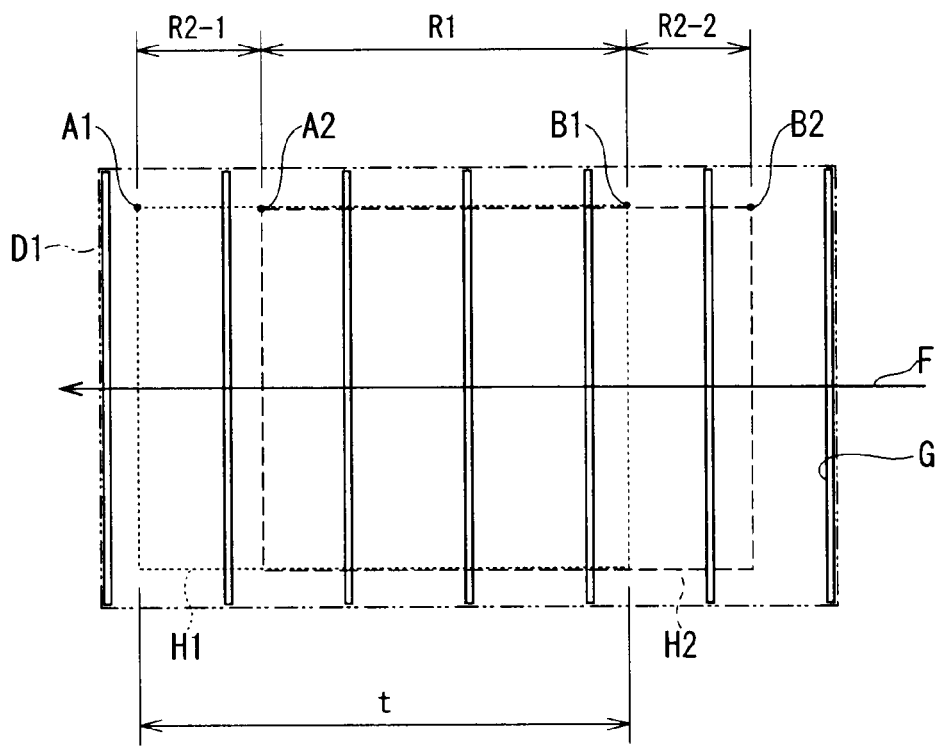
FIG. 2 is a view for explaining a first example of an image processing operation performed by an image processing unit included in the medical image display apparatus in FIG. 1.

FIG. 2 is a view for explaining a first example of an image processing operation performed by the image processing unit 8.

The volume data D1 is defined as the slice image group composed of the slice images G in the first example of an image processing operation. Further, the image such as the MPR image and the like is generated using only the slice image group data composed on the slice images G in the set a thickness range H, or using the aggregate of the slice image group data composed on the slice images G and the interpolated data which is calculated each time the thickness range H is set based on the slice image group.

Note that when the image such as the MPR image and the like is generated using the aggregate of the slice image group data and the interpolated data, a direction where data of each of slice images G included in the slice image group are aligned may accord with a thickness direction in the thickness range H, or may not accord with it. It is explained a case that the former direction accord with the latter direction as follows for an example.

As shown in FIG. 2, the image processing unit 8 provides, as one of the MPR functions, the thickness range H with a thickness in a visual axis direction F, projects a maximum value or a minimum value in voxel values along the thickness direction corresponding to respective pixels in the thickness range H (thickness ranges H1, H2, and the like), and generates the slice image group in the thickness range H as one image. Further, the image processing unit 8 moves (changes) a cross sectional position (slice position), that is, the thickness range H in the visual axis direction F little by little and continuously generates images such as MPR images and the like. At the time, a voxel value which is necessary between adjacent slice images G is automatically interpolated. The image processing unit 8 is composed of hardware (circuit) or/and software. Note that although a maximum value projecting method for projecting the maximum value is explained here as an example, a minimum value projecting method for projecting the minimum value is the same as the above method.

As shown in FIG. 2, the image processing unit 8 calculates the existing position (coordinate in the visual axis direction F) at which the maximum value of the voxel values along the thickness direction corresponding to the respective pixels in the slice image group in the thickness range H provided with the thickness in the visual axis direction from the cross sectional position exists. Next, the image processing unit 8 registers the calculated existing positions of the respective pixels to the thickness position table T1. The voxel values are luminance values (pixel values) of the volume data D1, and when the medical image generating apparatus is the X-ray CT apparatus, the voxel values are CT values.

Figure 3:
FIG. 3 is a view explaining a thickness position table generated by an image processing operation performed by an image processing unit included in the medical image display apparatus in FIG. 1.

FIG. 3 is a view explaining the thickness position table T1 generated by the image processing operation performed by the image processing unit 8.

The thickness position table T1 as shown in FIG. 3 is set by the image processing unit 8. The thickness position table T1 is thickness position information which shows the existing position at which the maximum value of the voxel values along the thickness direction corresponding to the respective pixels in the slice image group in the thickness range H, for example, in the thickness range H1 before movement. Note that the existing position of the maximum value is shown by, for example, a distance from a reference position (reference point). The existing position is stored, for example, each n×m pixels in the thickness position table T1. The value n×m shows image height×image width, that is, an image size. The unit of the existing position is, for example, [mm]. Further, the reference position is a start position of the thickness range H1 before movement. Various values such as a volume coordinate, a patient coordinate (reference position of a table-top), and the like can be used as the reference value of a coordinate showing the start position.

Returning to FIG. 2, the image processing unit 8 continuously generates images such as MPR images and the like according to the movement of the thickness range H along the visual axis direction, for example, according to the sliding movement of the thickness range H from the thickness range H1 on the rear side to the thickness range H2 on the front side in the visual axis direction F. The image processing unit 8 generates the image such as the MPR image and the like in the thickness range H1 by a conventional technology.

In contrast, when the image processing unit 8 generates the image such as the MPR image and the like in the thickness range H2 after movement, it first determines whether or not the thickness range H1 before movement overlaps the thickness range H2 after movement. Next, the image processing unit 8 divides the entire thickness range H1 before movement and the entire thickness range H2 after movement to an overlapping range R1 in which the thickness range H1 before movement overlaps the thickness range H2 after movement, a non-overlapping range R2-1 before movement which is the thickness range H1 before movement from which the overlapping range R1 is eliminated, and a non-overlapping range R2-2 after movement which is the thickness range H2 after movement from which the overlapping range R1 is eliminated according to the overlapping state of the thickness ranges H1 and H2.

At the time, the image processing unit 8 determines that the maximum value of the respective pixels, which is registered when the image such as the MPR image and the like in the thickness range H1 before movement are generated, exists in which of the overlapping range R1 and the non-overlapping range R2-1 before movement as to the each pixel based on the thickness position table T1. The image processing unit 8 determines the maximum value in the thickness range H2 after movement as to the respective pixels whose maximum value is determined to exist in the non-overlapping range R2-1 before movement referring to the slice image group in the thickness range H2 after movement (in the overlapping range R1 and the non-overlapping range R2-2 after movement). In contrast, the image processing unit 8 determines the maximum value in the thickness range H2 after movement as to the respective pixels whose maximum value is determined to exist in the overlapping range R1 referring to the maximum value corresponding to the thickness position table T1 and to the slice image group in the non-overlapping range R2-2 after movement. Then, the image processing unit 8 generates the image such as the MPR image and the like by projecting the maximum value which is determined to the respective pixels of the thickness range H2 after movement.

Since the function of the image processing unit 8 described above makes it unnecessary to refer to all the slice images G in the thickness range H2 after movement and thus the maximum value of the respective pixels of the thickness range H2 after movement can be simply calculated, a processing time for calculating data can be suppressed.

Note that the image processing unit 8 overwrites the existing position corresponding to the maximum value, which is determined to the respective pixels of the thickness range H2 after movement, to the thickness position table T1. Accordingly, when the image such as the MPR image and the like of a thickness range H3 (not shown) which is set after the thickness range H2 is generated, the image processing unit 8 generates the image of the thickness range H3 by dividing the thickness ranges H2 and H3 as described above.

To describe in more detail, the non-overlapping range R2-1 before movement is a range which is referred to when the image such as the MPR image and the like before movement are generated and is not referred to when the images after movement are generated. The overlapping range R1 is a range which is referred to when the images before movement are generated and is also referred to generate the images after movement. Further, the non-overlapping range R2-2 after movement is a range which is not referred to when the images before movement is generated and is referred to when the images after movement are generated. That is, as shown in FIG. 2, the non-overlapping range R2-1 before movement is the range from the start coordinate A1 of the thickness range H1 of the images generated before movement to the start coordinate A2 of the thickness range H2 of the images generated after movement. The overlapping range R1 is the coordinate from the start coordinate A2 of the thickness range H2 of the images generated after movement to the end coordinate B1 of the thickness range H1 of the images generated before movement. Further, the non-overlapping range R2-2 after movement is the coordinate from the end coordinate B1 of the thickness range H1 of the image generated before movement to the end coordinate B2 of the thickness range H2 of the images generated after movement. Note that the start coordinates A1, A2 and the end coordinates B1, B2 show positions in the visual axis direction F. Further, it is here assumed that the thickness range H1 before movement and the thickness range H2 after movement have the same thickness t.

Figure 4:
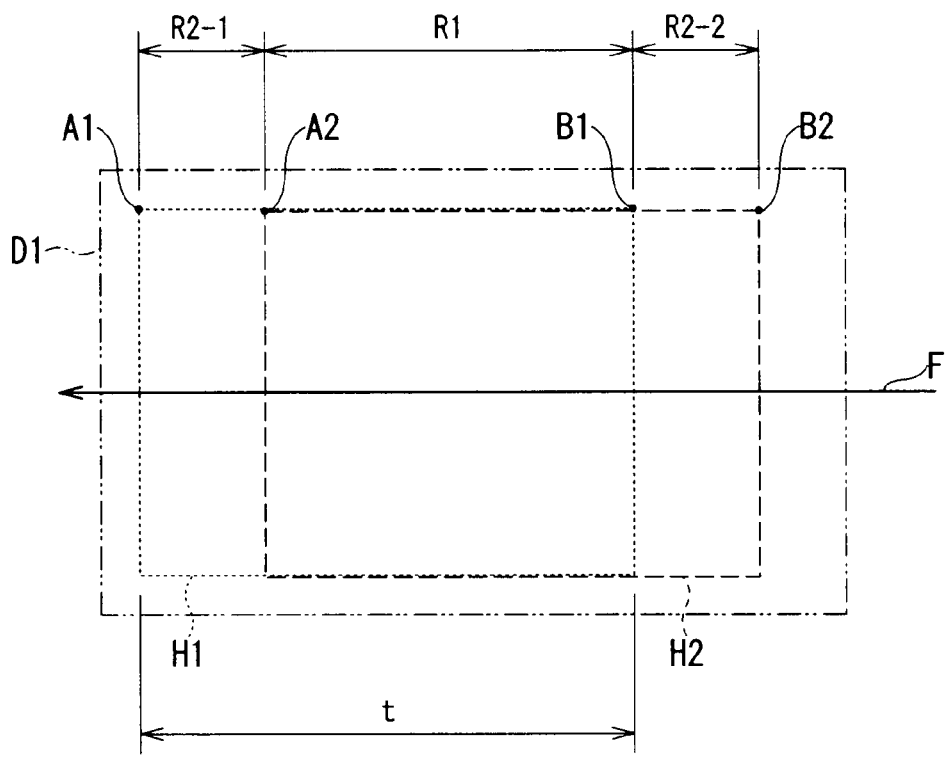
FIG. 4 is a view explaining a second example of an image processing operation performed by an image processing unit included in the medical image display apparatus in FIG. 1.

FIG. 4 is a view explaining a second example of the image processing operation performed by the image processing unit 8.

In the first example of the image processing operation of the image processing unit 8 shown in FIG. 2, the volume data D1 is defined as the slice image group data composed of the slice images G. In contrast, in the second example of image processing operation of the image processing unit 8 shown in FIG. 4, the volume data D1 is defined as the aggregate of the slice image group data composed of the slice images G and the interpolated data calculated based on the slice image group. The image such as the MPR image and the like are generated using an aggregate in the set thickness range H.

In a case of the image processing operation of image processing unit 8 to show in FIG. 4, it is suitable that the thickness range H is set with a multiple of a pixel size.

Note that when the volume data D1 is defined as the aggregate of the slice image group data and the interpolated data to show in FIG. 4, the slice image group are aligned may accord with a thickness direction in the thickness range H, or may not accord with it.

Next, an image display processing of the medical image display apparatus 1 described above will be explained. The controller 2 of the medical image display apparatus 1 performs an image processing by the image processing unit 8 and performs a display processing for displaying the images after the image processing. Note that it is explained the image processing operation of the image processing unit 8 to show in FIG. 2 for an example.

Figure 5:
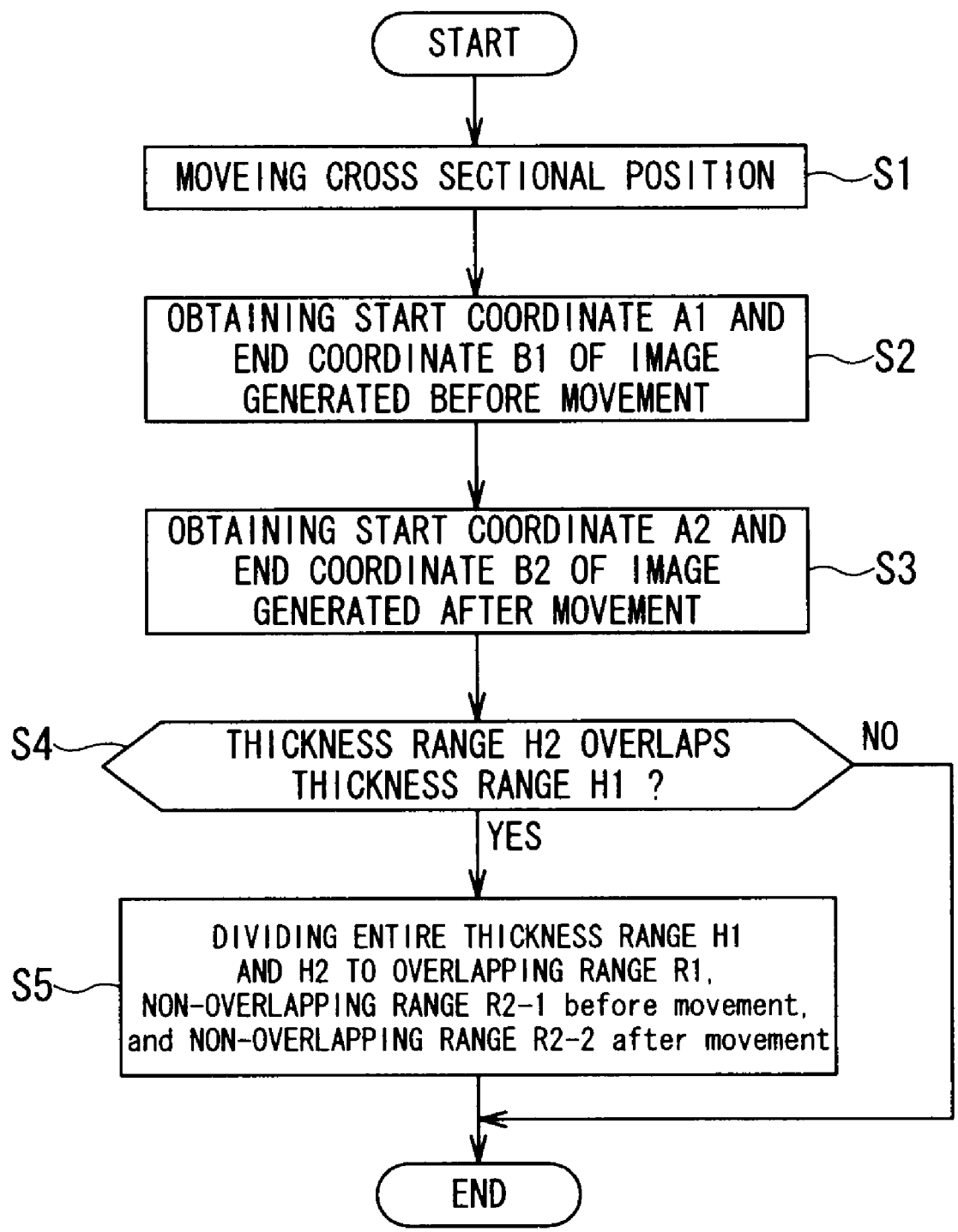
FIG. 5 is a flow chart showing steps of an image displaying operation performed by the medical image display apparatus in FIG. 1.

As shown in FIG. 5, the controller 2 moves the cross sectional position (slice position) in response to the input operation performed to the operation device 5 by the operator (step S1). With this operation, the thickness range H1 moves along the visual axis direction F and is made to the thickness range H2 (refer to FIG. 2).

Next, the controller 2 obtains the start coordinate A1 and the end coordinate B1 of the thickness range H1 of the images generated before movement (refer to FIG. 2) (step S2). Next, the controller 2 obtains the start coordinate A2 and the end coordinate B2 of the thickness range H2 of the images generated after movement (refer to FIG. 2) (step S3).

Thereafter, the controller 2 determines whether or not the thickness range H2 after movement overlaps the thickness range H1 before movement based on the obtained start coordinates A1, A2 and end coordinates B1, B2 (step S4). When, for example, the start coordinate A2 of the thickness range H2 after movement is smaller than the end coordinate B1 of the thickness range H1 before movement on the assumption that the coordinate increases from the rear side to the front side of the visual axis direction F (in the direction opposite to an arrow in FIG. 2), the controller 2 determines that the thickness range H1 before movement overlaps the thickness range H2 after movement. In contrast, when the start coordinate A2 of the thickness range H2 after movement is equal to or larger than the end coordinate B1 of the thickness range H1 before movement, the controller 2 determines that the thickness range H1 before movement does not overlap the thickness range H2 after movement.

When the controller 2 determines that the thickness range H2 after movement overlaps the thickness range H1 before movement (step S4; YES), the controller 2 divides the entire thickness range H1 before movement and the entire thickness range H2 after movement to the overlapping range R1 (range A2-B1 in FIG. 2), the non-overlapping range R2-1 before movement (range A1-A2 in FIG. 2), and the non-overlapping range R2-2 after movement (range B1-B2 in FIG. 2) (step S5) to thereby finish the processing. In contrast, when the controller 2 determines that the thickness range H2 after movement does not overlap the thickness range H1 before movement (step S4; NO), the controller 2 finishes the processing as it is. In this case, all the slice images G in the thickness range H2 after movement are referred to generate the MPR images.

Figure 6:
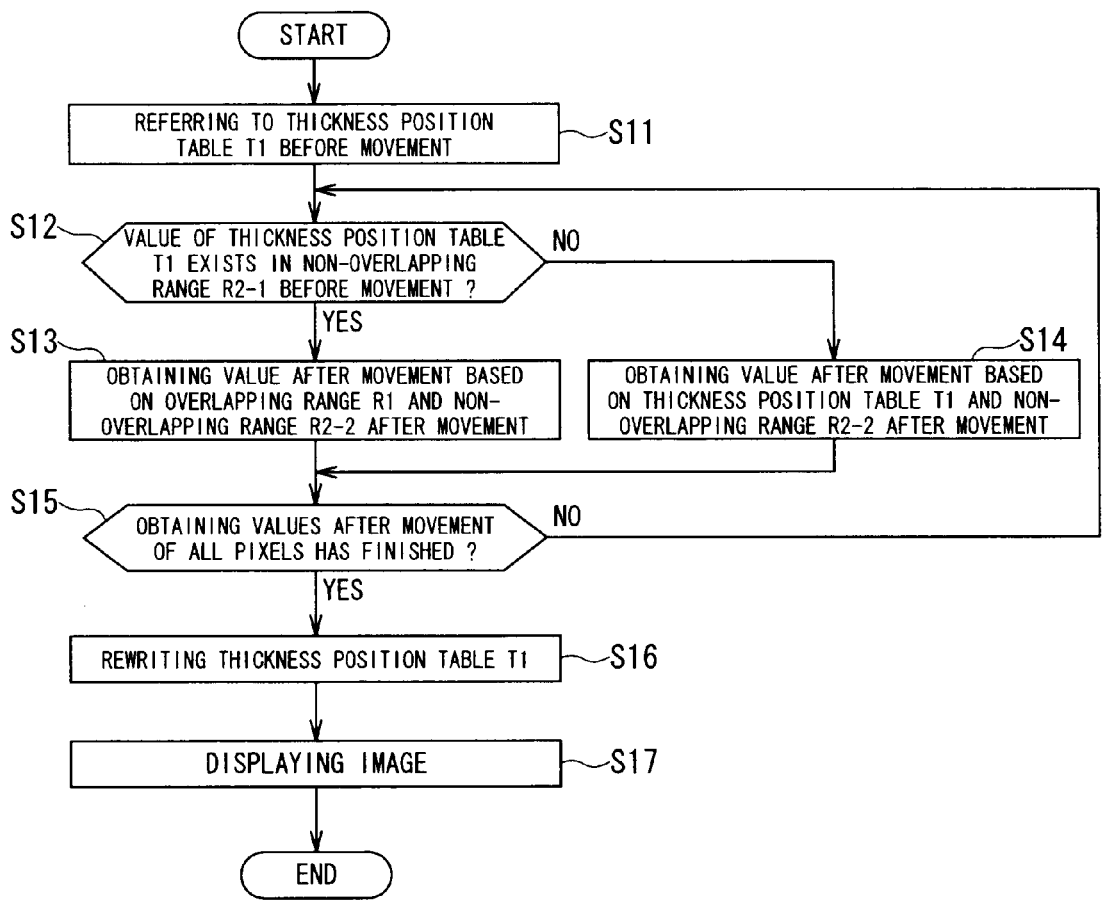
FIG. 6 is a flow chart showing steps of an image displaying operation performed by the medical image display apparatus in FIG. 1.

Thereafter, as shown in FIG. 6, the controller 2 refers to the thickness position table T1 before movement (step S11). Next, the controller 2 determines whether or not the existing position of the value of the thickness position table T1, that is, the maximum value of the respective pixels, which is registered when the image such as the MPR image and the like of the thickness range H1 before movement are generated, exists in the non-overlapping range R2-1 before movement (step S12). With this determination, as to the maximum value of the pixels, in which the controller 2 determines that the value of the thickness position table T1 exists in the non-overlapping range R2-1 before movement, the maximum value of the pixels corresponding to the existing position exists in the non-overlapping range R2-1 before movement. In contrast, as to the maximum value of the pixels, in which the controller 2 determines that the value of the thickness position table T1 does not exist in the non-overlapping range R2-1 before movement, the maximum value of the pixels corresponding to the existing position exists in the overlapping range R1. As a result, the controller 2 determines that the maximum value of the respective pixels exists in any of the non-overlapping range R2-1 before movement and the overlapping range R1.

When the controller 2 determines that the value of the thickness position table T1 exists in the non-overlapping range R2-1 before movement (step S12; YES), the controller 2 refers to the slice image group of the respective pixels in the thickness range H2 after movement (in the overlapping range R1 and in the non-overlapping range R2-2 after movement). Next, the controller 2 obtains the values after movement, that is, the maximum value after movement and the existing position of the maximum value of the respective pixels from the slice image group in the thickness range H2 after movement (step S13).

In contrast, when the controller 2 determines that the value of the thickness position table T1 does not exists in the non-overlapping range R2-1 before movement (step S12; NO), the controller 2 refers to the maximum value corresponding to the existing position of the thickness position table T1 and the slice image group in the non-overlapping range R2-2 after movement of the respective pixels. Next, the controller 2 obtains the value after movement, that is, the maximum value after movement and the existing position of the maximum value of the respective pixels (step S14).

Thereafter, the controller 2 determines whether or not the values after movement of all the pixels have been obtained (step S15) and waits until they have been obtained (step S15; NO). When the controller 2 determines that the values after movement of all the pixels have been obtained (step S15; YES), the controller 2 rewrites the existing positions of the thus obtained maximum values after movement of all the pixels to the thickness position table T1 before movement and rewrites the thickness position table T1 after it moves (step S16). Next, the controller 2 generates an image (MPR image) onto which the obtained maximum values after movement are projected, and causes the display device 4 to display the image (step S17).

With this operation, the image after movement is displayed on the display device 4 in place of the image before movement. As described above, images are continuously displayed on the display device 4 according to the movement of the cross sectional position in the visual axis direction F, that is, according to the movement of the thickness range H in the visual axis direction F. At the time, it is sufficient to compare the maximum value corresponding to the thickness position table T1 with the maximum value of the slice image group in the non-overlapping range R2-2 after movement as to the respective pixels whose maximum value exists in the overlapping range R1, and it is not necessary to refer to all the slice images G in the thickness range H after movement. With this operation, since the common portion of the base data of the image generated based on the thickness range H1 before movement and the image generated based on the thickness range H2 after movement can be effectively used and thus an amount of calculation for generating the image can be reduced, a processing time for calculating the data can be reduced.

As described above, according to the medical image display apparatus 1 of the first embodiment of the present invention, the entire thickness range H1 before movement and the entire thickness range H2 after movement are divided to the overlapping range R1, the non-overlapping range R2-1 before movement, and the non-overlapping range R2-2 after movement. Thereafter, the maximum value after movement of the pixels whose maximum value exists in the non-overlapping range R2-1 before movement is determined referring to the slice image group in the thickness range H2 after movement (in the overlapping range R1 and in the non-overlapping range R2-2 after movement). In contrast, the maximum value after movement of the pixels whose maximum value exists in the overlapping range R1 is determined referring to the maximum value corresponding to the existing position of the thickness position table T1 of the respective pixels and to the slice image group in the non-overlapping range R2-2 after movement.

As a result, according to the medical image display apparatus 1, as to the pixels whose maximum value exists in the overlapping range R1, since it is sufficient to compare the maximum value corresponding to the thickness position table T1 with the maximum value of the slice image group in the non-overlapping range R2-2 after movement, and it is not necessary to refer to all the slice images G in the thickness range H2 after movement, a calculate can be simplified. Thus, since the common portion of the base data of the images generated based on the thickness range H1 before movement and the images generated based on the thickness range H2 after movement can be effectively used and thus the amount of calculation for generating the image can be reduced. Therefore, since the processing time for calculating the data can be reduced, a display speed can be increased when an image is displayed according to the movement of the thickness range H. As a result, a diagnosis efficiency can be also improved.

Second Embodiment

A second embodiment of the medical image display apparatus according to the present invention will be explained referring to FIG. 7.

The second embodiment of the medical image display apparatus according to the present invention will be explained as to only a portion different from the first embodiment. Note that the explanation of a portion of the second embodiment, which is explained in the first embodiment, is omitted.

Figure 7:
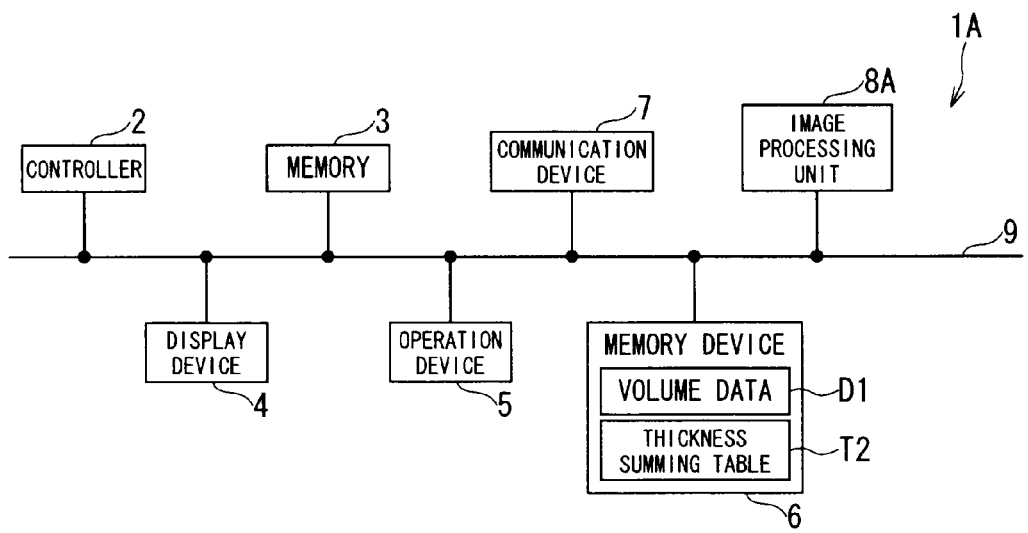
FIG. 7 is a block diagram showing a schematic arrangement of a second embodiment of a medical image display apparatus.

FIG. 7 is a block diagram showing a schematic arrangement of the second embodiment of the medical image display apparatus.

FIG. 7 shows the medical image display apparatus 1A of the second embodiment. As shown in FIG. 7, the medical image display apparatus 1A has an image processing unit 8A. As one of MPR functions, the image processing unit 8A provides a thickness range H (thickness ranges H1, H2, and the like) with a thickness in a visual axis direction F, and generates a slice image group (aggregate of slice images G) in the thickness range H as a sheet of image (MPR image) by projecting an average value of the voxel values along the thickness direction corresponding to respective pixels in the thickness range H. Further, the image processing unit 8A moves a cross sectional position (slice position), that is, the thickness range H in the visual axis direction F little by little and continuously generates images such as an MPR images and the like. Note that the average value of the voxel values along the thickness direction corresponding to the respective pixels is obtained by adding the voxel values of the slice image group of the respective pixels and dividing the added value by the thickness t.

Further, the image processing unit 8A calculates the total value of the voxel values along the thickness direction corresponding to the respective pixels in the slice image group in the thickness range H1 before movement and registers the total value of the voxel values along the thickness direction corresponding to the respective pixels to a thickness summing table T2. The thickness summing table T2 is stored to a storage device 6. Note that the thickness summing table T2 is total thickness information showing the total value of the voxel values along the thickness direction corresponding to the respective pixels in the slice image group in the thickness range H1 before movement. The thickness summing table T2 stores the total value of, for example, the respective pixels of n×m likewise the thickness position table T1 shown in FIG. 3.

The image processing unit 8A continuously generates images such as MPR images and the like according to the movement of the thickness range H along the visual axis direction, for example, according to the sliding movement of the thickness range H from the thickness range H1 before movement on a rear side to the thickness range H2 after movement on a front side in the visual axis direction F. At the time, the image processing unit 8A determines whether or not the thickness range H1 before movement overlaps the thickness range H2 after movement likewise the image processing unit 8 explained in the first embodiment. Next, the image processing unit 8A divides the entire thickness range H1 before movement and the entire thickness range H2 after movement to an overlapping range R1, a non-overlapping range R2-1 before movement, and a non-overlapping range R2-2 after movement according to the overlapping state of the thickness ranges.

When the overlapping range R1 does not exist, the image processing unit 8A determines the average value of the thickness range H2 after movement of the respective pixels referring to the slice image group in the thickness range H2 after movement (in the overlapping range R1 and in the non-overlapping range R2-2 after movement). In contrast, when the overlapping range R1 exists, the image processing unit 8A calculates the total value of the respective pixels in the slice image group in the thickness range H2 after movement by subtracting the total value of the respective pixels in the slice image group in the non-overlapping range R2-1 before movement from the total value of the voxel values along the thickness direction corresponding to the respective pixels of the thickness summing table T2 and adding the resultant value to the total value of the respective pixels in the slice image group in the non-overlapping range R2-2 after movement. Next, the image processing unit 8A determines the average value of the voxel values along the thickness direction after movement of the respective pixels by dividing the total value of the respective pixels calculated above by the thickness t of the thickness range H2 after movement. Then, the image processing unit 8A generates the image such as the MPR image and the like of the thickness range H2 after movement by projecting the average value determined to the respective pixels. At the time, since it is not necessary to refer to all the slice images G in the thickness range H2 after movement and thus the average value of the respective pixels of the thickness range H2 after movement can be calculated simply, a processing time for calculating data can be suppressed.

Further, the image processing unit 8A overwrites the total value determined to the respective pixels of the thickness range H2 after movement to the thickness summing table T2. Accordingly, the image such as the MPR image and the like of a thickness range H3 (not shown), which is set after the thickness range H2, is generated, it is assumed that the image processing unit 8A generates the image of the thickness range H3 by dividing the thickness range H2 and the thickness range H3 as described above.

As described above, according to the medical image display apparatus 1A of the second embodiment the present invention, the total value of the respective pixels in the slice image group in the thickness range H2 after movement is calculated by subtracting the total value of the respective pixels in the slice image group in the non-overlapping range R2-1 before movement from the total value of the voxel values along the thickness direction corresponding to the respective pixels of the thickness summing table T2 and adding the resultant value to the total value of the respective pixels in the slice image group in the non-overlapping range R2-2 after movement. Then, the average value of the voxel values along the thickness direction after movement of the respective pixels is determined by dividing the total value of the respective pixels calculated above by the thickness t of the thickness range H2 after movement. Accordingly, when the overlapping range R1 exists, it is not necessary to refer to all the slice images G in the thickness range H2 after movement and a calculate is simplified. Since the common portion of the base data of the images generated based on the thickness range H1 before movement and the images generated based on the thickness range H2 after movement can be effectively used and thus the amount of calculation for generating the image can be reduced. Since the processing time for calculating the data can be reduced, a display speed for displaying an image according to the movement of the thickness range H can be increased. As a result, a diagnosis efficiency can be also improved.

Other Embodiment

Note that the present invention is not limited to the embodiments described above and can be variously modified within the scope which does not depart from the gist of the present invention.

For example, although the cross sectional position, that is, the thickness range H is slidingly moved from the rear side to the front side of the visual axis direction F in the embodiments, the present invention is not limited thereto and the thickness range H may be slidingly moved from the front side to the rear side of the visual axis direction F and the sliding direction of the thickness range H is not limited.

Further, the thickness range H1 before movement and the thickness range H2 after movement have the same thickness t in the embodiments, the present invention is not limited thereto and the thickness ranges H1 and H2 may have a different thickness.

Finally, although the unit of the value stored to the thickness position table T1 is set to [mm] in the embodiments, the present invention is not limited thereto and various measures such as pixel and the like may be used.

What is claimed is:

1. A medical image display apparatus, comprising:
    a diagnostic image displaying unit configured to display a diagnostic image generated by voxel values in a predefined range formed along a predefined direction in volume data based on a slice image group;
    a range dividing unit configured to divide a range after changing into (1) an overlapping range in which the range after changing overlaps a range before changing, and (2) a non-overlapping range that does not include the overlapping range, when a position of the range before changing is changed in the predefined direction;
    a pixel value after changing setting unit configured to set a pixel value after changing (1) based on a pixel value constituting a diagnostic image before changing and voxel values along the predefined direction in the non-overlapping range according to a predefined condition when a position of a voxel value in the volume data corresponding to the pixel value constituting the diagnostic image before changing exists in the overlapping range, and (2) based on voxel values along the predefined direction in the range after changing according to the predefined condition when the position does not exist in the overlapping range, for each pixel constituting a diagnostic image after changing generated based on the voxel values along the predefined direction in the range after changing; and
    a diagnostic image generating unit configured to generate the diagnostic image after changing based on each pixel value after changing set by the pixel value after changing setting unit.

2. The medical image display apparatus according to claim 1, wherein the predefined condition is to obtain a maximum value of the voxel values along the predefined direction.

3. The medical image display apparatus according to claim 1, wherein the predefined condition is to obtain a minimum value in the voxel values along the predefined direction.

4. The medical image display apparatus according to claim 1, further comprising:
    a storage unit configured to store a coordinate in the predefined direction, the coordinate indicating where the voxel value corresponding to the pixel value constituting the diagnostic image before changing exists; and
    a writing unit configured to write the coordinate in the predefined direction, the coordinate indicating where the voxel value corresponding to the pixel value, set by the pixel value after changing setting unit, constituting the diagnostic image after changing exists.

5. The medical image display apparatus according to claim 1, wherein the pixel value after changing setting unit is configured to calculate interpolated data by interpolating based on slice image data included in the slice image group, and set the pixel value based on the slice image data and the interpolated data.

6. The medical image display apparatus according to claim 1, further comprising:
    a volume data generating unit configured to calculate interpolated data by interpolating based on slice image data included in the slice image group, and generate an aggregate of the slice image data and the interpolated data as the volume data,
    wherein the pixel value after changing setting unit sets is configured to set the pixel value based on the volume data generated by the volume data generating unit.

7. The medical image display apparatus according to claim 6, wherein the range, based on the diagnostic image, in the predefined direction is settable by a voxel measure.

8. The medical image display apparatus according to claim 1, wherein the predefined direction accords with a direction in which each slice image included in the slice image group is aligned.

9. A medical image display apparatus, comprising:
    a diagnostic image displaying unit configured to display a diagnostic image generated by voxel values in a predefined range formed along a predefined direction in volume data based on a slice image group;
    a range dividing unit configured to divide a range after changing into (1) an overlapping range that in which the range after changing overlaps a range before changing, and (2) a non-overlapping range that does not include the overlapping range, when a position of the range before changing is changed in the predefined direction;

a pixel value after changing setting unit configured to set a pixel value after changing based on a total value of voxel values along the predefined direction in the overlapping range according to a pixel value constituting a diagnostic image before changing, and based on a total value of voxel values along the predefined direction in the non-overlapping range, for each pixel constituting a diagnostic image after changing generated based on the voxel values along the predefined direction in the range after changing; and a diagnostic image generating unit configured to generate the diagnostic image after changing based on each pixel value after changing set by the pixel value after changing setting unit.

10. The medical image display apparatus according to claim 9, further comprising:

a storage unit configured to store the total value of voxel values along the predefined direction in the range before changing; and a writing unit configured to write the total value of the voxel values along the predefined direction in the range after changing.

11. The medical image display apparatus according to claim 9, wherein the pixel value after changing setting unit is configured to calculate interpolated data by interpolating based on slice image data included in the slice image group, and set the pixel value based on the slice image data and the interpolated data.

12. The medical image display apparatus according to claim 9, further comprising:

a volume data generating unit configured to calculate interpolated data by interpolating based on slice image data included in the slice image group, and generate an aggregate of the slice image data and the interpolated data as the volume data, wherein the pixel value after changing setting unit is configured to set the pixel value based on the volume data generated by the volume data generating unit.

13. The medical image display apparatus according to claim 12, wherein the range, based on the diagnostic image, in the predefined direction is settable by a voxel measure.

14. The medical image display apparatus according to claim 9, wherein the pixel value constituting the diagnostic image is an average value based on the total value of the voxel values in the predefined direction.

15. The medical image display apparatus according to claim 9, wherein the predefined direction accords with a direction in which each slice image included in the slice image group is aligned.

* * * * *